United States Patent
Pellikaan et al.

(10) Patent No.: US 9,308,175 B2
(45) Date of Patent: Apr. 12, 2016

(54) DOSAGE UNIT FOR SUBLINGUAL, BUCCAL OR ORAL ADMINISTRATION OF WATER-INSOLUBLE PHARMACEUTICALLY ACTIVE SUBSTANCES

(75) Inventors: Hubert Clemens Pellikaan, Utrecht (NL); Pieter Sebastiaan Vermeulen, Utrecht (NL); Johannes Caspar Mathias Elizabeth Bender, Utrecht (NL); Geert Feye Woerlee, Haarlem (NL)

(73) Assignee: Echo Pharmaceuticals B.V., Weesp (NL)

( * ) Notice: Subject to any disclaimer, the term of this patent is extended or adjusted under 35 U.S.C. 154(b) by 730 days.

(21) Appl. No.: 12/441,342

(22) PCT Filed: Sep. 14, 2007

(86) PCT No.: PCT/NL2007/050449
§ 371 (c)(1),
(2), (4) Date: Jul. 1, 2009

(87) PCT Pub. No.: WO2008/033024
PCT Pub. Date: Mar. 20, 2008

(65) Prior Publication Data
US 2010/0008985 A1    Jan. 14, 2010

(30) Foreign Application Priority Data

Sep. 15, 2006 (EP) .................................. 06120746

(51) Int. Cl.
A61K 9/10 (2006.01)
A61K 9/26 (2006.01)
A61K 9/20 (2006.01)
A61K 9/00 (2006.01)

(52) U.S. Cl.
CPC ............. *A61K 9/2077* (2013.01); *A61K 9/0056* (2013.01)

(58) Field of Classification Search
None
See application file for complete search history.

(56) References Cited

U.S. PATENT DOCUMENTS

| | | | |
|---|---|---|---|
| 4,719,239 A | 1/1988 | Muller et al. | |
| 4,840,799 A | 6/1989 | Appelgren et al. | |
| 5,057,319 A | 10/1991 | Gottwald et al. | |
| 5,234,927 A | 8/1993 | Galli Angeli et al. | |
| 5,292,650 A * | 3/1994 | Bonjouklian et al. | 435/121 |
| 5,342,625 A | 8/1994 | Hauer et al. | |
| 5,756,450 A | 5/1998 | Hahn et al. | |
| 6,054,136 A | 4/2000 | Farah et al. | |
| 6,086,915 A * | 7/2000 | Zeligs et al. | 424/455 |
| 6,248,363 B1 * | 6/2001 | Patel et al. | 424/497 |
| 6,634,576 B2 * | 10/2003 | Verhoff et al. | 241/21 |
| 6,730,330 B2 * | 5/2004 | Whittle et al. | 424/725 |
| 6,887,502 B2 | 5/2005 | Chen et al. | |
| 2003/0229027 A1 | 12/2003 | Eissens et al. | |
| 2004/0076126 A1 | 4/2004 | Klinksiek et al. | |
| 2004/0138293 A1 | 7/2004 | Werner et al. | |
| 2004/0229849 A1 | 11/2004 | Jost-Price et al. | |
| 2005/0008691 A1 | 1/2005 | Siles Ortega et al. | |
| 2005/0163843 A1 | 7/2005 | Boehm et al. | |
| 2009/0035379 A1 | 2/2009 | Stamm et al. | |
| 2010/0034888 A1 | 2/2010 | Pellikaan et al. | |

FOREIGN PATENT DOCUMENTS

| | | |
|---|---|---|
| AU | 784169 | 2/2006 |
| EP | 0 211 257 A2 | 2/1987 |
| EP | 0 631 782 A1 | 6/1994 |
| FR | 2758459 | 7/1998 |
| GB | 2 380 129 A | 4/2003 |
| WO | WO-93/13757 | 7/1993 |
| WO | WO-97/36577 A1 | 10/1997 |
| WO | WO-01/37808 A1 | 5/2001 |
| WO | WO-02/064109 A2 | 8/2002 |
| WO | WO-2004/069180 A2 | 8/2004 |
| WO | WO-2004/071645 A2 | 8/2004 |
| WO | WO-2005/004848 A1 | 1/2005 |
| WO | WO-2006/008092 | 1/2006 |
| WO | WO-2007/024133 A1 | 3/2007 |
| WO | WO-2007/072106 A1 | 6/2007 |
| WO | WO-2008/033023 A2 | 3/2008 |

OTHER PUBLICATIONS

CAS registry entry (No. 104987-11-3) for Tacrolimus, 2013.
CAS Registry entry (No. 50-23-7) for Hydrocortisone, 2013.
The HLB System a time-saving guide to emulsifier selection, ICI Americas Inc., 1980 (http://www.firp.ula.ve/archivos/historicos/76_Book_HLB_ICI.pdf).
CAS Registry No. 1972-08-3 entry for Tetrahydrocannabinol, 2013.
Dewey, "Cannabinoid Pharmacology", Pharmacological Reviews, 1986, vol. 38, No. 2, pp. 151-178.
Grotenhermen, "Cannabinoids for Therapeutic Use", Am J Drug Deliv, 2004, vol. 2, No. 4, pp. 229-240.

(Continued)

*Primary Examiner* — Tigabu Kassa
(74) *Attorney, Agent, or Firm* — Foley & Lardner LLP; Sunit Talapatra

(57) ABSTRACT

One aspect of the invention relates to a pharmaceutical dosage unit for sublingual, buccal, pulmonary or oral administration, said dosage unit having a weight of 20-500 mg and comprising 1-80 wt. % of a microgranulate that is distributed throughout a solid hydrophilic matrix; said microgranulate being characterized in that it: has a volume weighted average diameter of 5-100 m; contains at least 0.01 wt. %, preferably at least 0.1 wt. % of one or more water-insoluble pharmaceutically active substances; contains at least 10 wt. %, preferably at least 20 wt. % of an emulsifier component; and is capable of forming a micro-emulsion upon contact with saliva or water. The dosage units of the present invention achieve the inherent benefits of oral delivery while at the same time realizing a high transmucosal absorption rate of the cannabinoids contained therein. Other aspects of the present invention relate to the use of the aforementioned dosage units in the therapeutic or prophylactic treatment and to a process for the manufacture of said dosage units.

14 Claims, No Drawings

(56) References Cited

OTHER PUBLICATIONS

Hahn, et al. "Solid Surfactant Solutions of Active Ingredients in Sugar Esters", Pharmaceutical Research, 1989, vol. 6, No. 11, pp. 958-960.

Chambin O, et al. "Interest of Multifunctional Lipid Excipients: Case of Gelucire 44/14" Drug Development and Industrial Pharmacy, Jul. 2005, vol. 31, No. 6, pp. 527-534.

Franceschinis, et al. "Self-emulsifying pellets prepared by wet granulation in high-shear mixer: influence of formulation variables and preliminary study on the in vitro absorption" International Journal of Pharmaceutics, Mar. 3, 2005, vol. 291, No. 1-2, pp. 87-97.

International Search Report (PCT/NL2007/050448) dated Jul. 25, 2008.

ADM's "Lecithin Overview" available online May 10, 2005; www.adm.com/en-US/products/food/lecithin/Documents/Lecithin%20Overview.pdf.

Google date for ADM's Lecithin overview—printed 2014.

* cited by examiner

DOSAGE UNIT FOR SUBLINGUAL, BUCCAL OR ORAL ADMINISTRATION OF WATER-INSOLUBLE PHARMACEUTICALLY ACTIVE SUBSTANCES

This application is a United States Application under 35 U.S.C. 371 claiming benefit of PCT Application No. PCT/NL07/50449, filed on Sep. 14, 2007, which claims the benefit of EPO 06120746.0, filed on Sep. 15, 2006, the contents of each of which are incorporated herein by reference.

TECHNICAL FIELD OF THE INVENTION

The present invention relates to a pharmaceutical dosage unit for sublingual, buccal or oral administration that contains one or more water-insoluble pharmaceutically active substances and to the use of these dosage units in therapeutic or prophylactic treatment.

The invention also provides a process for the manufacture of the aforementioned dosage units.

BACKGROUND OF THE INVENTION

A sizeable fraction of the pharmaceutically active substances that is commercially available at present is very poorly soluble in water. As a result of this poor water solubility these pharmaceutically active substances are badly absorbed across mucosal barriers in e.g. the intestines and the mouth. This is why essentially water-insoluble pharmaceutically active substances are usually administered parenterally, e.g. intravenously, subcutaneously or intramuscularly. Since, however, these parenteral methods of administration are laborious and less suited for self-administration, efforts have been made by the pharmaceutical industry to find ways to deliver water-insoluble pharmaceutically active substances through a more convenient mode of administration, e.g. orally, sublingually or buccally.

It has been well recognised in the art of pharmacology that transmucosal absorption of water-insoluble substances can be enhanced significantly by providing these substances in the form of a very fine dispersion (e.g. an aqueos microemulsion) or by reducing the particle size of solid pharmaceutically active substances (e.g. by micronisation). In addition, the pharmaceutical industry has developed so called self-emulsifying preparations that spontaneously form a fine dispersion when contacted with water. Such self-emulsifying preparations may suitably be delivered via the oral mucosa (sublingual or buccal administration) or via the intestinal mucosa (e.g. oral administration).

Examples of water-insoluble pharmaceutically active substances include cannabinoids and particular classes of alkaloids. Cannabinoids are the active constituents of cannabis. Alkaloids occur as secondary metabolites in plants, animals (e.g. shellfish) and fungi. Many cannabinoids and alkaloids have demonstrable pharmacological effects in animals such as humans.

Cannabinoids, which are substituted meroterpenes are the major active constituents of the plant *Cannabis sativa*. The most important natural cannabinoid is the psychoactive tetrahydrocannabinol ($\Delta 9$-THC); others include the non-psychoactive (but pharmaceutically active) compounds cannabidiol (CBD) and cannabigerol (CBG). Cannabinoids can be administered by a variety of routes. Because of their high lipid solubility, topical administration is possible in such locations as the eye or the nasal mucosa. However, this has been of very limited applicability, because preparations of THC available in the past tended to be irritating to the eye. However, newer vehicles that permit lipid-soluble materials to be applied to the eye in aqueous solution may make this route of greater interest again.

In theory, percutaneous absorption, as from a drug-impregnated skin patch, should be possible, but the absorption would be very slow and not clinically useful.

Oral administration results in a slow and variable absorption, with a bioavailability of 10-20%, and usually less than 15%. Intravenous injection or infusion is possible, but because of the very low water-solubility of cannabinoids a special formulation must be used, such as a complex of the cannabinoid with plasma protein, or a solution in a water-miscible organic solvent. Intravenous administration of suitable preparations gives a very rapid onset of action, but because of dosage limitations to avoid excessive intensity of the peak effect, the duration of action is short.

Smoking is undoubtedly the best-known method of administration, and is the typical manner of using crude marijuana, as opposed to pure cannabinoids. Much of the total THC in crude cannabis is not free THC but tetrahydrocannabinolic acid. The heat just ahead of the advancing zone of combustion in a cigarette or pipeful of cannabis converts the THC acid to free THC, and volatilizes the THC so that it can be inhaled with the smoke, deep into the lung. The high lipid-solubility of the THC allows it to cross the alveolar membrane rapidly, entering the blood in the pulmonary capillaries. From here it is carried rapidly to the heart and pumped directly to the brain, so that the onset of action is at least as rapid as with intravenous injection.

What has been said above in relation to cannabinoids also applies by and large to many water-insoluble pharmaceutically active alkaloids and steroids. Alkaloids are usually classified by ether molecular feat, based on the metabolic pathway used to construct the molecule. When not much was known about the biosynthesis of alkaloids, they were grouped under the names of known compounds, or by the plant or animal they were isolated from. When more is learned about a certain alkaloids, the grouping is changed to reflect the new knowledge, usually taking the name of a biologically important amine that stands out in the synthesis process.

A steroid is a terpenoid lipid characterized by a carbon skeleton with four fused rings, generally arranged in a 6-6-6-5 fashion. Steroids can vary by the functional groups attached to these rings and the oxidation state of the rings. Hundreds of distinct steroids are found in plants, animals, and fungi. All steroids are biosynthetically derived either from the sterol lanosterol (animals and fungi) or the sterol cycloartenol (plants). Both sterols are derived from the cyclization of the triterpene squalene. Examples of pharmaceutically active steroids includes estrogens, progestogens, androgens.

Oral mucosal delivery offers several distinct advantages over other administration routes. The mouth is easily accessible with a wide aperture and a broad mucosal surface. The medication can pass easily into the reticulated veins that lie under the oral mucosa. The oral mucosa has more lipophilic cells than other mucosae, allowing for the delivery of lipophilic medications. It is found that medication absorbed through the buccal mucosa enters the circulation 4 to 8 times more rapidly than when it is ingested in pill or capsule form. Effects can be observed in 5-20 minutes compared to 30-60 minutes by ingestion into the stomach. Oral transmucosal delivery is also 20-30 times faster than transdermal (skin patch) delivery. Medication is more easily absorbed through the oral mucosa than through skin or rectal mucosa. Medication placed in the mouth is more acceptable to patients and more easily controlled than medication placed in the rectum, urethra, vagina, bladder, or up the nose.

GB 2 380 129 describes a pharmaceutical formulation for use in administration of a lipophilic medicament via a mucosal surface, which formulation comprises at least one lipophilic medicament and at least one self emulsifying agent, wherein upon hydration the formulation forms an emulsion containing the lipophilic medicament which is capable of adhering to a mucosal surface and allowing controlled release of the medicament. Also described are pharmaceutical formulation in the form of a gel or a compressed tablet for administration of a lipophilic medicament via the sublingual and/or buccal mucosa, wherein on contact with saliva the tablet or gel forms an emulsion containing the lipophilic medicament that adheres reversibly to the sublingual and/or buccal mucosa. Example 6 of the British patent application describes the preparation of a tablet for buccal or sublingual administration by dissolving glyceryl monostearate, polysorbate 80, ascorbyl palmitate and α-tocopherol and THC in alcohol, spraying the alcoholic solution onto a powder mix consisting of lactose and soluble starch, evaporating the alcohol, dusting the resulting granulate with talc and compressing to a target tablet weight of 101 mg.

Oral administration is generally seen as the most convenient mode of administration. Oral bioavailability, however, is greatly affected by the extent to which the pharmaceutically active substance is absorbed across the intestinal mucosa and the extent to which said substance is metabolised in the liver during the so called first pass.

Pulmonary administration via the respiratory system is also considered an efficient way of delivering pharmaceutically active substances. Administration occurs through inhalation of a nebula or aerosol carrying the active compound which can be taken up via the alveoli (lung).

WO 01/37808 describes solid pharmaceutical composition for improved delivery of hydrophilic or hydrophobic pharmaceutically active ingredients, said composition comprising a solid carrier that contains a substrate and an encapsulation coat on the substrate, wherein the encapsulation coat comprises at least one pharmaceutically active ingredient and at least one hydrophilic surfactant. The hydrophilic surfactant preferably is a surfactant having an HLB value of at least 10 or an ionic surfactant. It is stated in WO 01/37808 that the pharmaceutical composition can be formulated for oral, nasal, ocular, urethral, buccal, transmucosal, vaginal, topical or rectal delivery. It is further observed that hydrophilic surfactants can be used to provide increased solubility of the active ingredient in the solid carrier; improved dissolution of the active ingredient; improved solubilization of the active ingredient upon dissolution; enhances absorption and/or bioavailability of the active ingredient, particularly a hydrophilic active ingredient; and improved stability, both physical and chemical, of the active ingredient.

SUMMARY OF THE INVENTION

The inventors have developed a pharmaceutical dosage unit for sublingual, buccal, oral or pulmonary administration of water-insoluble pharmaceutically active substances that achieves the inherent benefits of these modes of administration whilst at the same time realising high transmucosal absorption of the pharmaceutically active substances contained therein. The dosage unit of the present invention has a weight of 20-500 mg and comprises 1-80 wt. % of a microgranulate that is distributed throughout a solid hydrophilic matrix; said microgranulate being characterised in that it:
  has a volume weighted average diameter of 5-100 μm;
  contains at least 0.01 wt. %, preferably at least 0.1 wt. % of one or more water-insoluble pharmaceutically active substances;
  contains at least 10 wt. % of an emulsifier component; and
  is capable of forming a micro-emulsion upon contact with saliva.

The dosage units of the present invention additionally offer the advantage that pharmaceutically active substances contained therein, such as Δ9-THC, are stabilised effectively against oxidation and/or isomerisation, even when the dosage unit is stored under ambient conditions for prolonged periods of time. Although the inventors do not wish to be bound by theory, it is believed that the pharmaceutically active substances are effectively encapsulated within the microgranulate and thus protected against degradation under the influence of light, temperature, oxygen, reactive hydrophilic ingredients and/or moisture. The emulsifier component of the dosage units of the present invention ensures that the microgranulate is quickly dispersed when it comes into contact with saliva or water. The resulting micro-emulsion is quickly absorbed by the buccal or sublingual mucosal tissue as well as by the intestinal mucosa.

The dosage units of the present invention can be manufactured by simply combining the microgranulate component with the matrix ingredients, i.e. without the use of organic solvents such as alcohol.

Accordingly, another aspect of the invention relates to process for the manufacture of a dosage unit for buccal, sublingual or oral administration as described above, said process comprising:
  thoroughly mixing 5 to 80 parts by weight of a microgranulate having a volume weighted average diameter of 5-100 μm and containing at least 0.1 wt. % of one or more water-insoluble pharmaceutically active substances and at least 10 wt. % of an emulsifier component with 20-95 parts of a matrix forming composition; and
  shaping the resulting mixture.

DEFINITIONS

The term "microgranulate" as used herein refers to a particulate material that consists of small discrete particles. The discrete particles within the microgranulate contain both the emulsifier component and the one or more water-insoluble pharmaceutically active substances.

The term "water-insoluble" as used herein means that a substance has a solubility in demineralised water of 37° C. (neutral pH) of less than 200 mg/l.

The term "cannabinoid" as used herein encompasses the following substances: Δ-8 tetrahydrocannabinol, Δ-9-tetrahydrocannabinol, cannabidiol, olivetol, cannabinol, cannabigerol, nabilone, Δ-9-tetrahydro cannabinotic acid, 3-dimethylnepty 11 carboxylic acid homologine 8 as well as the prodrugs and pharmaceutically acceptable salts of these cannabinoids.

The term "tetrahydrocannabinol" or "THC" unless indicated otherwise, refers to Δ-9-tetrahydrocannabinol.

The term "alkaloid" as used herein encompasses substances belonging to one of the following groups of alkaloids:
  piperidine group (e.g. coniine, nicotine)
  pyrrolidine group (e.g. hygrine, nicotine)
  tropane group (e.g. atropine, cocaine)
  quinoline group (e.g. quinine, strychnine)
  isoquinoline group (e.g. morphine, codeine)
  phenylethylamine group (e.g. mescaline, ephedrine, dopamine)
  indole group (e.g. tryptaimines, such as serotonine)
  purine group (e.g. xanthines, such as caffeine)
  vinca alkaloids (e.g. vinblastine)

The term "steroid" as used herein refers to a terpenoid lipid that comprises a carbon skeleton with four fused rings, arranged in a 6-6-6-5 fashion The term "emulsifier component" as used herein refers to a surface active component comprising one or more substances having a polar or ionic portion and a non-polar, e.g. aliphatic portion, which surface active component is capable of stabilising an emulsion, especially an oil-in-water emulsion. It is noted that the present invention encompasses the use of an emulsifier containing two or more surface active substances, notably a combination of an O/W emulsifier and a co-emulsifier.

The term "O/W emulsifier" as used herein refers to a surface active component that facilitate oil-in-water emulsification. Typically, O/W emulsifiers exhibit an HLB-value of at least 8.

The term "co-emulsifier" as used herein refers to a surface active component with hydrophobic character that is capable of enhancing the oil-in-water emulsification properties of an O/W emulsifier with which it is combined. Typically, co-emulsifiers exhibit an HLB value of 3-7.

DETAILED DESCRIPTION OF THE INVENTION

One aspect of the invention relates to a pharmaceutical dosage unit for sublingual, buccal or oral administration, said dosage unit having a weight of 20-500 mg and comprising 1-80 wt. % of a microgranulate that is distributed throughout a solid hydrophilic matrix; said microgranulate being characterised in that it:
  has a volume weighted average diameter of 5-100 μm;
  contains at least 0.01 wt. %, preferably at least 0.1 wt. % of one or more water-insoluble pharmaceutically active substances;
  contains at least 10 wt. %, preferably at least 20 wt. % of an emulsifier component; and
  is capable of forming a micro-emulsion upon contact with saliva or water.

Microemulsions are identifiable as possessing one or more, preferably all of the following characteristics:
  They are formed spontaneously or substantially spontaneously when their components are brought into contact, that is without substantial energy supply, e.g. in the absence of heating or the use of high shear equipment or other substantial agitation.
  They exhibit thermodynamic stability.
  They are substantially non-opaque, i.e. are transparent or opalescent when viewed by optical microscopic means.
  Microemulsions comprise a dispersed or particulate (droplet) phase, the particles of which are of a size less than 2,000 A°.

The release characteristics of the dosage unit as well as the stability of the water-insoluble pharmaceutically active substances are affected by the average diameter of the microgranulate. Preferably, the present granulate has a volume weighted mean average diameter of at least 8 μm, more preferably of at least 10 μm. The volume weighted mean average diameter of the granulate preferably does not exceed 80 μm, more preferably it does not exceed 70 μm. The volume weighted mean diameter of the granulate may suitably be determined by means of image analysis methods.

The microgranulate in the present dosage unit typically consists of regularly shaped granules, meaning that the average ratio between the maximum and minimum diameter of the granules is preferably within the range of 1 to 4, more preferably in the range of 1 to 3 and most preferably in the range of 1 to 2.

The present dosage unit advantageously contains at least 5 wt. %, most preferably at least 10 wt. % of the microgranulate. According to a particularly preferred embodiment, the present microgranulate contains at least 0.5 wt. %, most preferably at least 1 wt. % of one or more water-insoluble pharmaceutically active substances.

According to a particularly preferred embodiment, the dosage unit of the present invention contains between 0.05 and 20 wt. %, more preferably between 0.5 and 20 wt. % and most preferably between 1 and 10 wt. % of water-insoluble pharmaceutically active substances.

The amount of one or more water-insoluble pharmaceutically active substances contained in the dosage unit typically exceeds 10 μg. Preferably, said amount is in the range of 0.1-100 mg, more preferably of 0.5-100 mg and most preferably of 1-50 mg.

The microgranulate in the present dosage unit advantageously contains at least 50 wt. % even more preferably at least 75 wt. % of the emulsifier component. The emulsifier component may suitably comprise a mixture of two or more emulsifiers, e.g. a mixture of an emulsifier and a co-emulsifier.

According to a particularly preferred embodiment, the water-insoluble pharmaceutically active substances and the emulsifier component together represent at least 60 wt. %, more preferably at least 80 wt. % and most preferably at least 90 wt. % of the microgranulate. Besides the water-insoluble pharmaceutically active substances and the emulsifier component, the microgranulate may suitably contain other components such as anti-oxidants, preservatives, fat, wax, further pharmaceutically active substances, etc.

The stability of the water-insoluble pharmaceutically active substances in the present dosage unit may be further enhanced by the inclusion of an anti-oxidant. According to a preferred embodiment, the dosage unit contains at least 10 ppm, preferably at least 50 ppm of an anti-oxidant selected from the group consisting of vitamin C, vitamin E, vitamin A, flavonoids, polyphenols, and combinations thereof. According to an even more preferred embodiment, at least 80%, more preferably at least 90% of the aforementioned anti-oxidant is contained within the microgranulate.

The benefits of the present invention are particularly marked when water-insoluble pharmaceutically active substance has a solubility in demineralised water of 37° C. of less than 100 mg/l, most preferably of less than 20 mg/l.

The dosage units of the present invention are particularly suitable for delivering pharmaceutically active cannabinoids or alkaloids. Cannabinoids employed in the present dosage unit are preferably selected from the group consisting of Δ-8-tetrahydrocannabinol, Δ-9-tetrahydrocannabinol, cannabidiol, tetrahydrocannabinovarin, cannabidivarin and combinations thereof. Most preferably, the present dosage unit contains at least 0.1 wt. % of Δ-9-tetrahydrocannabinol. Even more preferably, the present dosage unit contains 0.3-50 mg of Δ-9-tetrahydrocannabinol, most preferably 0.5-30 mg of Δ-9-tetrahydrocannabinol.

Alkaloids that may advantageously be employed in the present dosage unit include codeine, morphine, quinine, quinoline, atropine, vinblastine, vincristine, respirine, ergotamine, scopolamine, veratrine, heroin and fentanyl.

Steroids that may suitably be employed include the estrogens 17α-ethinylestradiol, esters and ethers of 17α-ethinylestradiol, 17α-ethinylestradiol 3-dimethylamino propionate, 17α-ethinylestradiol 3-cyclopentyl ether (quienestrol) and 17α-ethinylestradiol 3-methyl ether (mestranol), estrone, estradiol and estriol, and their esters, conjugated equine estrogens; the progestogens progesterone, desogestrel, norgestimate, gestodene, dydrogesterone, medroxyprogesterone acetate, norethynodrel, norethinedrone, norethinedrone acetate, levonorgestrel, dl-norgestrel, cyproterone acetate, chlormadinone acetate, magestrol acetate, 17 D-acetyl norgestimate, dienogest, trimegestone, drosperinone and nomagestrel; and the androgens testosterone, testosterone esters and dehydroepiandrosterone.

The solid hydrophilic matrix of the present dosage unit typically contains less than 15 wt. % of water. Even more preferably, the water content of the dosage unit does not exceed 10 wt. %, most preferably said water content does not exceed 2 wt. %.

In order to facilitate rapid absorption of the water-insoluble pharmaceutically active substances by the oral mucosal tissue a muco-adhesive agents are advantageously incorporated in the present dosage unit. Preferably, the hydrophilic matrix of the dosage unit contains 0.1-20 wt %, more preferably 0.1-5% of a muco-adhesive agent. The muco-adhesive agent is advantageously selected from the group consisting of carbomers, cellulose derivates, plant lectin, dextrin, hypromellose, chitosan, polyethylene oxide, alginate and combinations thereof. A mucoadhesive agent exhibits the property of adhering to a biological tissue, for example to a mucus membrane in the buccal cavity and of being maintained there for a more or less lengthy period of time. The mucoadhesion phenomenon is described in the literature and is provided by the establishment of binding between one or more mucoadhesive compounds of the pharmaceutical dosage form and functional chemical groups present at the surface of the biological tissue. The interactions which are involved in the mucoadhesion mechanism are described as being of physical mechanical or chemical nature. Suitable examples of mucoadhesive agents include carbomers, cellulose derivates, plant lectin, dextrin, hypromellose, chitosan, polyethylene oxide, alginate and combinations thereof.

In order for the water-insoluble pharmaceutically active substances to be released rapidly, the hydrophilic matrix of the present dosage unit must disintegrate quickly when it comes into contact with saliva. Disintegration of the hydrophilic matrix is facilitated by the incorporation of a disintegrant. Preferably, the hydrophilic matrix contains 1-15 wt. %, more preferably 1-10 wt. % and most preferably 2-6 wt. % of a disintegrant. Examples of disintegrants that may suitably be employed in the present dosage unit include crospovidone, croscarmellose sodium, sodium starch glycolate, hydroxypropyl cellulose, polacrilin potassium, pregelatinized starch, microctystalline cellulose and combinations thereof.

The dosage units of the present invention may also advantageously contain a gas generating reactant mixture, e.g. a mixture of sodium bicarbonate and an acid. Upon contact with water the components within the reaction mixture will generate a gas, e.g. carbon dioxide, thus accelerating in-mouth disintegration of the dosage unit.

The solid dosage units of the present inventions are conveniently produced in a tabletting machine. In order to enable easy removal of the tablets from the moulds, typically the hydrophilic matrix of the dosage unit contains 0.1-10% of a lubricant. Preferably, the lubricant is selected from the group consisting of talc, sodium stearyl fumarate, magnesium stearate, calcium stearate, hydrogenated castor oil, hydrogenated soybean oil, polyethylene glycol and combinations thereof.

The manufacture of the present dosage units is further facilitated by incorporating silica in the hydrophilic matrix. Advantageously, the hydrophilic matrix contains 0-5 wt. %, preferably 0.1-0.5 wt. % of silica.

According to a particularly preferred embodiment, the dosage unit of the present invention comprises a combination of silica, disintegration agent, muco-adhesive agent and lubricant, said combination representing at least 70 wt. %, preferably at least 80 wt. % of the hydrophilic matrix.

The present invention encompasses the use of a large variety of emulsifier components. Preferably, the emulsifier component employed in according to the present invention comprises a non-ionic emulsifier.

According to another preferred embodiment, the emulsifier component comprises an emulsifier in the form of an ester containing 1 to 4 $C_{6-24}$ fatty acid residues. These fatty acid residues are comprised in the lipophilic part of the emulsifier. Furthermore, the emulsifier component advantageously comprises an emulsifier that contains at least one free hydroxyl group, preferably at least two free hydroxyl groups. The free hydroxyl groups are comprised in the hydrophilic part of the emulsifier.

The hydrophilicity and lipophilicity are different among emulsifiers, and the balance between the two is called HLB value. HLB-values can range from 0 to 20. An emulsifier with higher lipophilicity shows a lower HLB whereas higher hydrophilicity has is reflected in a higher HLB. According to a particularly, preferred embodiment, the emulsifier component comprises an O/W emulsifier with an HLB-value of more than 7, more preferably of at least 8, even more preferably of at least 10 and most preferably of at least 12. Typically, the HLB-value of the O/W emulsifier does not exceed 18.

In addition the aforementioned O/W emulsifier, the emulsifier may suitably comprise a co-emulsifier with an HLB of 3-7, especially with an HLB of 3.5-6.5. Typically, the O/W emulsifier is contained in the present dosage unit in an amount of 50-99% by weight of the microgranulate. The co-emulsifier is preferably contained in the dosage unit in an amount of 0-50% by weight of the microgranulate.

According to a particularly preferred embodiment, the emulsifier component is selected from the group consisting of sugar fatty acid esters, mono-glycerides, diglycerides, diacetyl tartaric acid ester of monoglyceride, polyglycerol esters, diacetyl tartaric acid ester of diglyceride, calcium stearoyl lactylate, sodium stearoyl lactylate and combinations thereof. Even more preferably, the emulsifier component is selected from the group consisting of sugar fatty acid esters, polyglycerol esters and combinations thereof. Even more preferably, the emulsifier component is a sugar fatty acids ester, especially a sugar fatty acid ester containing 1-3 fatty acid residues per molecule. Most preferably, the sugar fatty acid ester employed as emulsifier component contains 1 fatty acid residue per molecule. The sugar residue in the aforementioned sugar fatty acid esters most preferably is a sucrose residue.

According to a particularly preferred embodiment, the emulsifier component contains at least 50%, most preferably at least 90% by weight of the microgranulate of a sucrose fatty acid ester, especially a sucrose fatty acid ester containing 1-3 fatty acid residues per molecule.

The dosage unit of the present invention may suitably take the shape of a compressed tablet. Such a tablet may suitably comprise two or more layers of different composition.

Advantageously, the dosage unit exhibits a certain level of porosity in order to allow easy water access. Typically, the dosage unit of the present invention exhibits a porosity of 1-50%, preferably of 2-15%.

Another aspect of the present invention relates to the use of water-insoluble pharmaceutically active substances for the manufacture of a medicament for use in therapeutic or prophylactic treatment, said treatment comprising sublingual, buccal or oral administration of a dosage unit as described herein before. Dosage units according to the present invention that contain one or more cannabinoids are particularly suited for sublingual or buccal administration. Dosage units containing one or more alkaloids are particularly suited for oral administration since due to their bitter taste alkaloids are preferably not delivered by sublingual or buccal administration.

The dosage units of the present invention advantageously contain one or more cannabinoids. These cannabinoid containing dosage units are particularly suitable for use in the treatment of psychotic disorders, epilepsy, movement disorders, eating disorders, Alzheimer, stroke, multiple sclerosis, spinal cord injury, peripheral neuropathy, neurogenic pain or nausea. Furthermore, said dosage units may advantageously be used as a sedative or a sedative-enhancer in combination treatments.

Yet another aspect of the invention relates to a process for the manufacture of a pharmaceutical dosage unit, especially a dosage unit for buccal, sublingual or oral administration, said dosage unit having a weight of 20-500 mg and comprising 5-80 wt. % of a microgranulate that is distributed throughout a solid hydrophilic matrix, said process comprising:

thoroughly mixing (i) 5 to 80 parts by weight of a microgranulate having a volume weighted average diameter of 5-100 μm and containing at least 0.1 wt. % of one or more water-insoluble pharmaceutically active substances and at least 10 wt. % of an emulsifier component with (ii) 20-95 parts of matrix-forming components; and shaping the resulting mixture so as to obtain the dosage unit.

The manufacturing process of the present invention offers the advantage that it is very easy to operate as is does not employ elevated temperatures, emulsification or organic solvents. The microgranulate employed in the present process is advantageously obtained from a precipitation process in which a pumpable emulsion comprising a continuous phase of a polar solvent and a dispersed phase containing the emulsifier component and the water-insoluble pharmaceutically active substances is combined with an extractant comprising a supercritical, subcritical or liquefied gas; said solvent being substantially more soluble in the extractant than said emulsifier. As the solvent is extracted from the emulsion the formation of microgranules containing the emulsifier component and the water-insoluble pharmaceutically active substances will start to occur. This particular precipitation process enables the production of a microgranulate under extremely mild conditions (no elevated temperature, no oxygen). Thus, the process of the present invention enables the production of dosage units under very mild conditions, meaning that degradation of the water-insoluble pharmaceutically active substances during processing can be minimised very effectively.

The microgranulate employed in the present process may suitably contain lipophilic components that melt at elevated temperatures. Preferably, the temperatures employed during the mixing and shaping are sufficiently low to ensure that the microgranulate does not melt, thereby ensuring that the particulate nature of the microgranulate is retained in the final dosage unit. Typically, the present process does not employ temperature in excess of 60° C. More preferably, said process does not employ temperatures in excess of 50° C., or even in excess of 40° C.

According to a particularly preferred embodiment, the microgranulate is a free flowing powder. Preferably, the microgranulate has a volume weighted mean average diameter of at least 8 μm, more preferably of at least 10 μm. The volume weighted mean average diameter of the granulate preferably does not exceed 80 μm, more preferably it does not exceed 70 μm.

The shaping of the mixture of microgranulate and matrix-forming components preferably comprises compression of said mixture in a mould, followed by removal of the shaped dosage unit from said mould.

The invention is further illustrated by means of the following examples

EXAMPLES

Example 1

A microgranulate containing tetrahydrocannabinol (THC) was prepared as follows. Sucrose monolaurate (HLB=15) and THC were heated under a stream of nitrogen till 120° C. The THC to sucrose monolaurate ratio was 1:15 by weight. After thoroughly mixing, the putty-like melt was saturated with $CO_2$ (and thereby softened) following one of either method below:

The warm melt was poured into a 120° C.-preheated autoclave and brought to 250 bars. The autoclave was pressurized with carbon dioxide using a plunger pump (LeWa) and heated by means of a jacket, using heating oil. The lump was further liquefied through saturation with $CO_2$ by stirring the melt in the supercritical $CO_2$ for al least 30 mins using a Büchi™ magnetic stirrer.

The melt was chilled to −20° C. and crushed to obtain maximum surface area. To this end a −20° C. pre-cooled mortar was used in an inert and dry atmosphere. The obtained powder was poured into a 60° C. pre-warmed autoclave and brought to 250 bars. The autoclave was pressurized with carbon dioxide using a plunger pump (LeWa) and heated by means of a jacket, using heating oil. The vessel was further heated to 120° C. with heating oil and hot $CO_2$ (120° C.) under continuous stirring allowing optimal $CO_2$-dissolvation.

After terminating the stirring, the melt was allowed to settle at the bottom of the autoclave. The valve at the bottom of the autoclave was opened. The high pressure in the autoclave forced the melt through a 120° C.-heat traced pipe into a 120° C.-heat traced 340 μm nozzle (Spraying Systems Inc). Powder was formed upon depressurization from 250 bars to atmospheric pressure. The microgranulates had an average diameter of 30 μm as determined by light microscopy.

A tabletting powder for direct compression was mixed using the following ingredients:

50 mg of the microgranulate
4 mg $SiO_2$ (aerosil)
15 mg sodium starch glycolate (Primojel™)
60 mg $NaHCO_3$
50 mg citric acid (1 aq.)

The powder was compressed applying a 15 kN force to obtain a 10 mm tablet with a total weight of 129 mg. The tablet strength was 40 N and the tablet disintegrated in 60 seconds in water of 37° C., forming a micro emulsion.

The powder mixing and tabletting was performed in a dry and inert atmosphere.

Example 2

A tabletting powder for direct compression was mixed using the following ingredients;

50 mg of the microgranulate described in Example 1
4 mg SiO2 (aerosil)
15 mg sodium starch glycolate (Primojel™)
30 mg $NaHCO_3$
30 mg sodium alginate
50 mg citric acid (1 aq.)

The powder was compressed applying a 15 kN force to obtain a 10 mm tablet with a total weight of 179 mg. The tablet strength was 40 N and the tablet disintegrated in 70 seconds in water of 37° C., forming a micro emulsion.

Example 3

A tabletting powder for direct compression was mixed using the following ingredients:
5 g of the microgranulate described in Example 1
10 g maltodextrin
5 g lactose
2 g sodium starch glycolate (Primojel™)
0.05 g aerosil
0.05 g magnesium stearate.

The powder was compressed applying a 15 kN force to obtain 7 mm tablets with a total weight of 60 mg. The tablet strength was 25 N and the tablet disintegrated in 5 minutes in water of 37° C., forming a micro emulsion.

Example 4

A tabletting powder for direct compression was mixed using the following ingredients:
5 g of the microgranulate described in Example 1
15 g sorbitol
0.2 g magnesium stearate.

The powder was compressed applying a 15 kN force to obtain 7 mm tablets with a total weight of 60 mg. The tablet strength was 40 N and the tablet disintegrated in 4½ minutes in water of 37° C., forming a micro emulsion.

Example 5

A microgranulate containing THC was prepared as follows. Xylitol was heated till 125° C. on a magnetic hot plate stirrer with a magnetic stir bar. Sucrose monolaurate (Synthapharm Surfhope D-1216; HLB=16.8) was suspended into the melt using an Ultra Turrax homogenizer. The xylitol to sucrose monolaurate ratio was 5:1 by weight. THC in a concentration of 2.5% (w/w) was added to the previous melt under constant stirring. The formulation was allowed to cool down for at least 3 hours. During the first hour of the cooling-traject the melt was repeatedly turned over with a spoon. The solidified product was crushed into pieces and ground with a "rotating blades-type" grinder. The resulting microgranulate had an average size value of 20 μm.

Example 6

A tabletting powder for direct compression was mixed using the following ingredients:
61 mg of the microgranulate described in Example 5
18 mg of Lactose
8 mg of AcDiSol (carboxymethylcellulose sodium)
2 mg of Aerosil The powder was compressed applying a 15 kN force to obtain a 10 mm tablet with a total weight of 258 mg containing 2.3 mg of THC. The tablet strength was 40 N and the tablet disintegrated in 2 minutes in water of 37° C., forming a micro emulsion. The powder mixing and tabletting was performed in a dry and inert atmosphere.

The pharmacokinetics of the tabletting powder was studied via an in-vivo test in one healthy human subject (n=1). The test person was treated with one-single dose of 7 mg by taking 3 tablets. Plasma samples were drawn from the test person at regular intervals. The levels of THC and their metabolites 11-COOH-THC and 11-OH-THC were measured via LC-MS.

The results are given in Table 1 in which they are compared with the data obtained for pulmonary administration of vaporised Tetranabinex® (inhalation route) and sublingual spray of Sativex®.

TABLE 1

Pharmacokinetic of THC levels administered via sublingual tablets compared with the vaporised method (inhalation route) and the sublingual spray Sativex produced by GW Pharma.

| | Concentration THC in (ng/ml) | | |
|---|---|---|---|
| Time (min) | Sublingual dosage unit | Vaporised Tetranabinex ®* (THC BDS) | Oro-mucosal Sativex ®* |
| 0 | 0.00 | 0.00 | 0.00 |
| 7 | 20.19 | 64.14 | 0.00 |
| 16 | 33.58 | 108.70 | 0.01 |
| 30 | 68.03 | 62.00 | 0.07 |
| 48 | 6.68 | 31.00 | 0.23 |
| 69 | 8.68 | 19.50 | 0.40 |
| 97 | 11.50 | 13.30 | 0.84 |
| 196 | 18.87 | 4.50 | 2.04 |
| 318 | 4.73 | 2.25 | 1.40 |
| 508 | 5.68 | 0.70 | 0.49 |
| 1440 | 1.02 | 0.23 | 0.06 |

*data source: GW pharma

The relevant pharmacokinetic data of the developed sublingual tablet are:
maximum serum concentration ($C_{max}$) of 70 ng/ml,
Tmax which is the time between dose and $C_{max}$ was 33 min.
Bioavailability was 150% compared to the inhalation route.

The second broad peak in the serum THC-9 concentration observed after almost 200 minutes shows that a substantial fraction of the THC was absorbed in the intestines. This illustrates the oral bioavailability of the THC contained in the tablet.

Example 7

A tabletting powder for direct compression was mixed using the following ingredients:
37 mg of the microgranulate described in Example 5
25 mg Sorbitol
78 mg Lactose monohydrate
2 mg Mg-stereate
5 mg Aerosil ($SiO_2$)
4 mg Primojel The powder was compressed applying a 15 kN force to obtain a 7 mm tablet with a total weight of 150 mg. The tablet strength was 40 N and the tablet disintegrated in 7 min in water of 37° C., forming a micro emulsion.

The powder mixing and tabletting was performed in a dry and inert atmosphere.

Example 8

Microgranulate containing THC was prepared according to GW Pharma patent (WO 02/064109). For this procedure, GmS (Somerset Cosmetic, Renton, Wash., USA), Tween 80 (Fluka), Ascorbic acid 6-palmitate (Sigma) and Vitamin E (Fluka) in a weight ratio of (50:5:1:1) respectively, were poured in 100 parts of ethanol and stirred during 48 h to obtain a stable non-transparent emulsion. Simultaneously, 8 parts of lactose (Arnold Suhr) and 1 part of soluble starch (ASC-reagent, Sigma) were mixed by rotation end over end and sieved through a 0.30 mesh. Then, 2 grams of THC were added to 10.3 grams of the emulsion and the final solution was poured into an spraying device (Precision valve Corp. Yonkers N.Y.).

Next, from 20 cm height, 36 grams of lactose/starch mix was slowly passed through an 0.42 mm sieve, creating a continuous and unbroken flow of powder during 26 seconds. Simultaneously, the THC emulsion was sprayed into the flow of powder 5 cm under the sieve (at a distance of ~7.5 cm's), also in exactly 26 seconds. During this operation the sieve was zig-zagged over a sheet of paper to prevent coated particle to stick to earlier coated particles. The granulate formed was allowed to dry. After drying, the granulate was sieved over a 0.42 mm sieve in order to remove agglomerates.

The granulate, designated as the GW-product, so obtained was compared to the microgranulate described in example 5.

The microgranulate of Example 5, when added in an amount of 50 mg could be dispersed completely in 1-3 minutes in 50 ml water (25° C.), yielding an opalescent dispersion with no visible particles which remained stable for days. In contrast, when the same test performed with the GW-product, even after 30 minutes of stirring, it was not possible to disperse the microgranulate.

The invention claimed is:

1. An oral pharmaceutical dosage unit comprising 1-80 wt. % of microgranulate particles distributed throughout a solid hydrophilic matrix, wherein the microgranulate particles have a volume weighted average diameter of 10-100 μm and consist of:
   (a) at least 0.5 wt. % of one or more cannabinoids having a solubility in demineralised water of 37° C. (neutral pH) of less than 200 mg/l;
   (b) at least 50 wt. % of sugar fatty acid esters with an HLB of more than 7; and, optionally
   (c) an anti-oxidant, preservative, fat, wax, additional active substance and/or co-emulsifier,
   wherein the one or more cannabinoids and sugar fatty acid esters together represent at least 80 wt. % of the microgranulate; and
   wherein the pharmaceutical dosage unit forms a microemulsion upon contact with saliva or water.

2. The pharmaceutical dosage unit according to claim 1, wherein the dosage unit has between 0.5 and 10 wt. % of the cannabinoids.

3. The pharmaceutical dosage unit according to claim 1, wherein the dosage unit has 0.5-100 mg of the cannabinoids.

4. The pharmaceutical dosage unit according to claim 1, wherein the dosage unit has at least 10 μg of the cannabinoids.

5. The pharmaceutical dosage unit according to claim 1, wherein the microgranulate has at least 10 wt. % of the sugar fatty acid esters with an HLB of at least 10.

6. The pharmaceutical dosage unit according to claim 1, wherein the sugar fatty acid esters is a sucrose fatty acid ester.

7. The pharmaceutical dosage unit according to claim 6, wherein the sucrose fatty acid ester is 1-3 fatty acid residues per molecule.

8. The pharmaceutical dosage unit according to claim 1, wherein the cannabinoid is a tetrahydrocannabinoid.

9. The pharmaceutical dosage unit according to claim 1, wherein the solid hydrophilic matrix is 0.1-20 wt. % of a mucoadhesive agent selected from the group consisting of carbomers, cellulose derivatives, plant lectin, dextrin, hypromellose, chitosan, polyethylene oxide, alginate and combinations thereof.

10. The pharmaceutical dosage unit according to claim 8, wherein the dosage unit has 1-50 mg of the cannabinoids.

11. The pharmaceutical dosage unit according to claim 1, wherein the microgranulate has a volume weighted mean particle size of 10-180 μm.

12. The pharmaceutical dosage unit according to claim 1, wherein the dosage unit is a compressed tablet.

13. The pharmaceutical dosage unit according to claim 1, suitable for sublingual, buccal, or pulmonary delivery.

14. The pharmaceutical dosage unit according to claim 1 consisting of 5-80 wt. % of the microgranulate and 20-95 wt. % matrix forming components.

* * * * *